（12）United States Patent
Bezemer et al.

(10) Patent No.: US 6,500,193 B1
(45) Date of Patent: Dec. 31, 2002

(54) SUTURES

(75) Inventors: Jeroen Mattijs Bezemer, Utrecht (NL); Joost Robert de Wijn, Nijmegen (NL); Jan Nieuwenhuis, Gorinchem (NL)

(73) Assignee: IsoTis N.V., Bilthoven (NL)

( * ) Notice: Subject to any disclaimer, the term of this patent is extended or adjusted under 35 U.S.C. 154(b) by 194 days.

(21) Appl. No.: 09/614,265

(22) Filed: Jul. 12, 2000

(30) Foreign Application Priority Data

Jul. 12, 1999 (EP) .............................. 99202280

(51) Int. Cl.[7] .............................................. A61L 17/00
(52) U.S. Cl. ....................... 606/228; 528/354
(58) Field of Search ................. 606/228, 230, 606/231; 528/271, 272, 308.1, 354, 355, 359

(56) References Cited

U.S. PATENT DOCUMENTS

| | | | | |
|---|---|---|---|---|
| 2,092,512 A | * | 9/1937 | Hermann et al. ............ 606/230 |
| 3,908,201 A | | 9/1975 | Jones et al. ..................... 3/1 |
| 4,224,946 A | | 9/1980 | Kaplan ..................... 128/335.5 |
| 4,246,904 A | | 1/1981 | Kaplan ..................... 128/335.5 |
| 4,621,638 A | * | 11/1986 | Silvestrini ................... 606/230 |
| RE32,770 E | * | 10/1988 | Kaplan ......................... 606/231 |
| 5,102,419 A | | 4/1992 | Gertzman et al. ........... 606/228 |
| 5,476,909 A | * | 12/1995 | Kim et al. .................... 528/354 |
| 5,508,036 A | * | 4/1996 | Bakker et al. .............. 128/899 |
| 5,522,841 A | * | 6/1996 | Roby et al. ................. 528/354 |
| 5,902,875 A | * | 5/1999 | Roby et al. ................. 528/354 |
| 5,919,893 A | * | 7/1999 | Roby et al. ................. 606/228 |
| 5,980,948 A | * | 11/1999 | Goedemoed et al. ........ 424/489 |
| 2001/0051832 A1 | * | 12/2001 | Bakker et al. ............ 623/23.58 |

FOREIGN PATENT DOCUMENTS

WO WO 00/59559 * 10/2000

* cited by examiner

Primary Examiner—Rodney M. Lindsey
(74) Attorney, Agent, or Firm—Banner & Witcoff, Ltd.

(57) ABSTRACT

The invention relates to a suture comprising a copolymer of a polyethylene glycol terephtalate and a polybutylene terephtalate, which copolymer comprises 45–60 wt. %, based on the weight of the copolymer, of the polyethylene glycol terephtalate, and 55–40 wt. %, based on the weight of the copolymer, of the polybutylene terephtalate.

11 Claims, 1 Drawing Sheet

SUTURES

Figure 1:
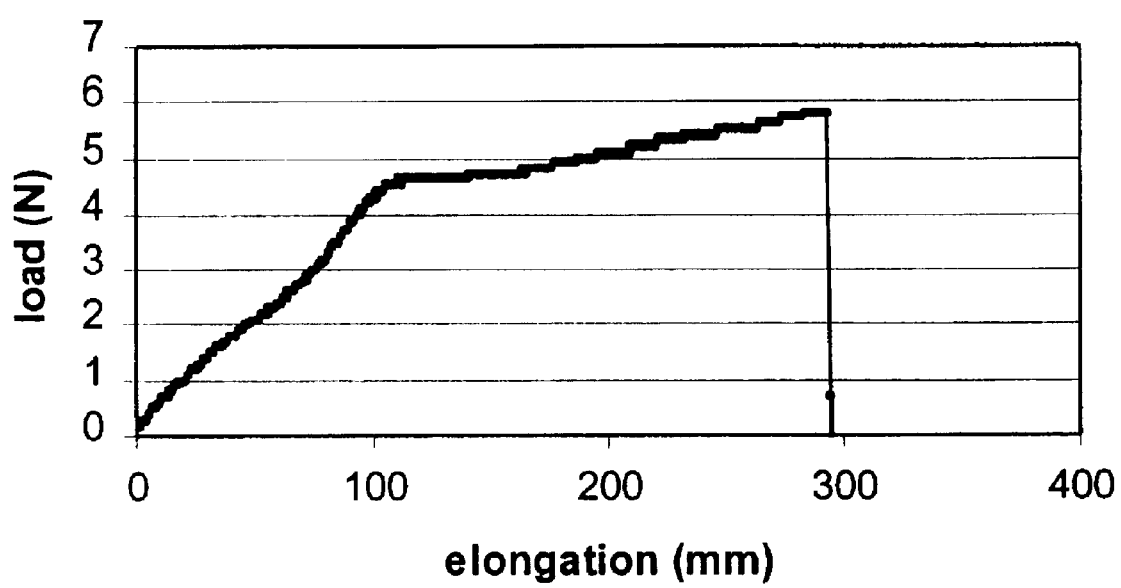

The invention relates to the field of surgical aids. More in particular, the invention relates to sutures.

Sutures are composed of threads or threadlike materials used for keeping tissue together. They may be applied in the skin of victims of accidents in order to repair large wounds. They may also be used internally, usually during or after surgery. In the latter case, usually other types of tissue are to be stitched together, such as muscle tissue.

Conventionally, sutures have been manufactured of non-degradable materials like nylon and polypropylene or degradable materials like polyglycolic acid and copolymers of glycolic acid and lactic acid. These materials are sufficiently biocompatible to keep risks of infections and the like within acceptable limits. On the other hand, they are sufficiently strong to fulfil their purpose.

A disadvantage of the non-degradable conventional sutures is that they have to be removed after a certain time period, usually when the wound is recovered to such an extent that stitches are no longer necessary. In the case of external uses, this forms a nuisance in the form of a return visit to a physician. In the case of internal uses of sutures, this forms a more significant problem.

In U.S. Pat. No. 4,224,946, a non-absorbable surgical suture is disclosed, which is derived from segmented polyether-ester block copolymers. The copolymers comprise a soft and a hard block. The soft block may for instance be a (tetramethylene ether)glycol and has a number average molecular weight of 500–3,000. The hard block may for instance be a diacid, such as terephtalic acid or 1,4-cyclohexanedicarboxylic acid. The hard block is preferably present in an amount of 50–85% in the copolymer. The overall number average molecular weight of the copolymer is 25–30,000. As mentioned, the described suture is non-absorbable, which means that it does not degrade in vivo.

The U.S. Pat. No. 5,102,419 discloses a surgical suture material comprising segmented copolyether/esters. The copolymers contain soft and hard segments. In the examples, the copolymers are prepared from 1,4-butanediol, dimethyl phtalate and polytetramethylene ether glycol. Thus, the hard segments are butylene terephtalate blocks, and the soft segments are non-hydrophilic polytetramethlene ether terephtalate segments. The amount in which the soft segment is present in the copolymer is 40% or lower. The weight average molecular weight of the soft segment is preferably 1,000.

In the past, biodegradable sutures have been developed. These decompose in the tissue environment of the patient, desirably after a time when wound recovery has occurred to an extent that their strength is no longer necessary. This constitutes a large improvement in comfort for patients, as they do not have to return to a physician to have their stitches removed.

Biodegradable polymers that are used for the manufacture of commercially available sutures are polyglycolides and polylactides. Although these materials have an adequate degradability profile, they do not leave much room for variation. Different circumstances for application of sutures demand different properties. Important properties that have to be adjusted, depending on the type of application of a suture, are knot strength, slip, tensile strength, pliability and the like. It has been found that, using polyglycolides and polylactides, it is difficult to design a suture having the desired property profile, although a large amount of variation is possible by copolymerizing lactic acid and glycolic acid, as well as the copolymerization with other alfa-hydroxy acid members.

The present invention aims to provide a novel suture of a biodegradable, biocompatible material, which does not have the problems of the conventional sutures.

Surprisingly, it has been found that these goals may be reached by using a specific copolymer for manufacturing a suture. Accordingly, the invention relates to a suture comprising a copolymer of a polyethylene glycol terephtalate and a polybutylene terephtalate, which copolymer comprises 45–60 wt. %, based on the weight of the copolymer, of the polyethylene glycol terephtalate, and 55–40 wt. %, based on the weight of the copolymer, of the polybutylene terephtalate.

The suture of the invention is highly biocompatible and has a very good biodegradability. By choosing the ratio of the polyethylene glycol terephtalate and the polybutylene terephtalate, and by choosing the molecular weights of both constituents, it is possible to fine-tune the properties of the suture. Thus, the material provides a well-defined manoeuvring space for obtaining a suture having properties required for a certain application.

In general, the properties of the suture may be varied as follows. Higher amounts of polyethylene glycol terephtalate in the material, while keeping the amount of the polybutylene terephtalate constant, lead to a higher elasticity of the suture, and to a lower knot strength. Another parameter by which the properties of the suture can be varied, is the molecular weight of the constituents of the copolymer. Using a polyethylene glycol terephtalate for preparing the copolymer having a higher molecular weight, will increase the flexibility of the suture.

As has been mentioned, the material on which the present suture is based, is a copolymer of a polyalkylene glycol and aromatic polyester. The copolymer comprises 45–60 wt. %, preferably 50–55 wt. % of the polyethylene glycol terephtalate, and 55–40 wt. %, preferably 50–45 wt. % of the polybutylene terephtalate. These ratios are selected in order to achieve on the one hand a good flexibility, and on the other hand a favourable degradation behaviour. The group of block copolymers forms a preferred type of copolymers according to the invention.

Preferably, the polyethylene glycol terephtalate has a weight average molecular weight of about 150 to about 600, more preferably of about 200 to about 500. It has been found that the use of a polyethylene glycol terephtalate having a weight average molecular weight within the indicated ranges provides a suture having an excellent (i.e. low) swellability and stretching behaviour. An increase in weight average molecular weight of this component may have the effect that the suture swells too much in vivo and may be too elastic. Also, the suture might degrade too fast for some applications.

The weight average molecular weight of the copolymer preferably lies between about 10,000 and 200,000, more preferably between about 50,000 and about 120,000. Even more preferably the weight average molecular weight of the copolymer lies between about 70,000 and about 90,000 which corresponds roughly to a number average molecular weight between about 35,000 and 45,000. In general, the properties of a suture improve when the weight average molecular weight of the copolymer increases, until an optimal situation has been reached.

The weight average molecular weight may suitably be determined by gel permeation chromatography (GPC). This technique, which is known per se, may for instance be performed using chloroform as a solvent and polystyrene as external standard. Alternatively, a measure for the weight average molecular weight may be obtained by using viscometry (see NEN-EN-ISO 1628-1). This technique may for instance be performed at 25° C. using chloroform as a solvent. Preferably, the intrinsic viscosity of the copolymer lies between 0.2289 and 1.3282 dL/g, which corresponds to a weight average molecular weight between 10,000 and 200,000. Likewise, the more preferred ranges for the weight average molecular weight measured by GPC mentioned above can also be expressed in terms of the intrinsic viscosity.

The preparation of the copolymer will now be explained by way of an example. Based on this description, the skilled person will be able to prepare any desired copolymer within the above-described class. An alternative manner for preparing these copolymers is disclosed in U.S. Pat. No. 3,908,201.

A polyethylene glycol terephtalate/polybutylene terephtalate copolymer may be synthesized from a mixture of dimethyl terephtalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene. In this step the polyethyene glycol substantially does not react. After transesterification, the temperature is raised slowly to about 245° C., and a vacuum (finally less than 0.1 mbar) is achieved. The excess butanediol is distilled and a prepolymer of butanediol terephtalate condenses with the polyethylene glycol to form a polyethylene/polybutylene terephtalate copolymer. A terephtalate moiety connects the polyethylene glycol units to the polybutylene terephtalate units of the copolymer and thus such copolymer is sometimes also referred to as a polyethylene glycol terephtalate/polybutylene terephtalate copolymer (PEGT/PBT copolymer).

The copolymer described above may conveniently be processed into a desired shape using any known manner such as extrusion, and so forth. The objective shape and size will depend on the envisaged application of the suture. Suitable examples of methods that can be used to prepare sutures of the copolymer are described in U.S. Pat. Nos. 5,102,419 and 4,246,904, the contents of which are incorporated herein by reference, for different polymers.

The suture can either be formed into a mono-filament type suture or into a multifilament braided type suture. For the mono-filament suture types, the sutures may be prepared by straight extrusion of pellets of the copolymer, after which needle(s) might be attached to a certain length of the suture. In order to prepare a multifilament yarn, the copolymer may be processed by spinning into a multifilament yarn and subsequent braiding, using conventional polymer processing equipment. The suture preferably consists of a thread having a thickness between 0.01 and 1 mm.

In a preferred embodiment, a suture according to the invention is a monofilament suture. In comparison with a multifilament suture, this type of suture has significantly smaller surface area per unit length of the thread. Thus, the risk of infection is significantly reduced. It is a great advantage of the invention, that a monofilament suture has sufficient mechanical strength for most applications.

The invention will now be elucidated by the following, non-restrictive example.

EXAMPLE

A copolymer derived from polyethylene glycol (MW 300), 1,4-butanediol and dimethyl terephthalate, having about 55 weight % poly(ethylene glycol)-terephthalate (PEGT) units and 45 weight % poly(butylene terephthalate) (PET) units, was extruded and drawn into a 0.28 mm monofilament, analogous to the procedures described in U.S. Pat. Nos. 5,102,419 and 4,246,904. The intrinsic viscosity of the copolymer was 0.64 dL/g.

Physical properties of the resulting filaments are determined according to European Pharmacopeia Suppl. 2000, pp. 1228–1231). A typical curve, showing the mechanical properties of a 70 cm long suture containing a simple knot, is presented in FIG. 1.

In table 1, the results of the testing of five sutures prepared as set forth above are presented. It is noticed that the properties of the sutures are in line with the requirements set in the European Pharmacopeia.

TABLE 1

| Diameter (mm) | | | Minimum breaking load (N) | | | Elongation at break (%) | | |
|---|---|---|---|---|---|---|---|---|
| min. | max | average | min. | max. | average | min. | max. | average |
| 0.263 | 0.268 | 0.266 | 4.8 | 5.8 | 5.2 | 20 | 42 | 30 |

What is claimed is:

1. A suture comprising a copolymer of a polyethylene glycol terephthalate and a polybutylene terephthalate, which copolymer comprises 45–60 wt. %, based on the weight of the copolymer, of the polyethylene glycol terephthalate, and 55–40 wt. %, based on the weight of the copolymer, of the polybutylene terephthalate.

2. A suture according to claim 1, wherein the weight average molecular weight of the polyethylene glycol terephthalate is from 150 to 600.

3. A suture according to claim 2, wherein the weight average molecular weight of the polyethylene glycol terephthalate is from 200 to 500.

4. A suture according to claim 1, wherein the weight average molecular weight of the copolymer is from 10,000 to 200,000.

5. A suture according to claim 4, wherein the weight average molecular weight of the copolymer is from 50,000 to 120,000.

6. A suture according to claim 1 having a monofilament structure.

7. The use of a copolymer a copolymer of a polyethylene glycol terephthalate and a polybutylene terephthalate for manufacture of a suture, which copolymer comprises 45–60 wt. %, based on the weight of the copolymer, of the polyethylene glycol terephthalate, and 55–40 wt. %, based on the weight of the copolymer, of the polybutylene terephthalate.

8. The use of a suture according to claim 1 for stitching wounds.

9. An apparatus useful in stitching tissue together comprising a suture including a copolymer comprising about 45 weight percent to about 60 weight percent of polyethylene glycol terephthalate and about 40 weight percent to about 55 weight percent of polybutylene terephthalate.

10. A method of making an apparatus useful in stitching tissue together comprising forming a copolymer comprising about 45 weight percent to about 60 weight percent of polyethylene glycol terephthalate and about 40 weight percent to about 55 weight percent of polybutylene terephthalate into a suture.

11. A method of treating a wound comprising stitching tissue together using a suture including a copolymer comprising about 45 weight percent to about 60 weight percent of polyethylene glycol terephthalate and about 40 weight percent to about 55 weight percent of polybutylene terephthalate.

* * * * *